United States Patent
Murphy et al.

(10) Patent No.: US 6,626,445 B2
(45) Date of Patent: Sep. 30, 2003

(54) CART FOR SURGICAL CONSOLE

(75) Inventors: Brian G. Murphy, Mission Viejo, CA (US); Earl F. Robinson, Lake Forest, CA (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/863,688

(22) Filed: May 23, 2001

(65) Prior Publication Data

US 2001/0035702 A1 Nov. 1, 2001

Related U.S. Application Data (63) Continuation-in-part of application No. 29/114,834, filed on Dec. 2, 1999, now Pat. No. Des. 447,567.
(60) Provisional application No. 60/241,120, filed on Oct. 17, 2000.

(51) Int. Cl.$^7$ ................................................ A61B 19/02
(52) U.S. Cl. ................................ 280/47.34; 312/249.8; 312/209; 606/34
(58) Field of Search ............................. 312/209, 249.8, 312/223.1, 250, 223.6, 223.2; 606/34; 280/47.34

(56) References Cited

U.S. PATENT DOCUMENTS

| | | | |
|---|---|---|---|
| 4,095,859 A | * | 6/1978 | Decker et al. ............... 312/209 |
| 4,359,085 A | * | 11/1982 | Mueller ....................... 165/135 |
| D280,762 S | | 9/1985 | LaCelle et al. .............. D24/17 |

(List continued on next page.)

FOREIGN PATENT DOCUMENTS

| EP | 0 424 686 A1 | 5/1991 |
|---|---|---|

OTHER PUBLICATIONS

CooperVision Surgical brochure for the Master, Series Ten Thousand™, Copyright 1986, 8 pages.
CooperVision Surgical brochure for the KCP™ Phaco–Emulsifier®, Copyright 1986, 2 pages.
CooperVision Surgical brochure for the CooperVision System VI™, Copyright 1986, 2 pages.
CooperVision Surgical brochure for the Series Ten Thousand® Ocutome® Vitroeoretinal Systems, Copyright 1988, 2 pages.
CooperVision Surgical brochure for the Cavitron/Kelman® Model 6500 E.I.S.™ and the Model 7500 I/A System III™ with AVIT™, Copyright 1983, 6 pages.
CooperVision Surgical brochure for the Ocutome® Model 8800/Fragmatome® Model 8300, Copyright 1986, 2 pages.
CooperVision Surgical brochure for the Cavitron/Kelman® Phaco–Emulsifier® Aspirator, Model 9001, Copyright 1985, 2 pages.
CooperVision Surgical brochure for the Cavitron/Kelman® Phaco–Emulsifier® Aspirator Model 8001, Copyright 1985, 2 pages.
"Operation Manual for Storz Premiere Microsurgical Systems," 1988, 84 pages.

(List continued on next page.)

*Primary Examiner*—Brian L. Johnson
*Assistant Examiner*—Kelly E Campbell
(74) *Attorney, Agent, or Firm*—W. David Lee (57) ABSTRACT

An improved cart for a surgical console. The cart includes a base, an internal frame coupled to the base, and an external housing substantially encasing the internal frame. The external housing comprises a single piece of molded plastic. The external housing prevents operating room fluid ingress into the internal frame. Therefore, the internal frame, its various portions, and the various electronic apparatus and consumables that are stored therein are protected from corrosion and damage.

1 Claim, 9 Drawing Sheets

U.S. PATENT DOCUMENTS

| | | | |
|---|---|---|---|
| 4,607,897 A | * 8/1986 | Schwartz | 248/188.7 |
| D285,484 S | 9/1986 | LaCelle et al. | D24/1.1 |
| D286,325 S | 10/1986 | LaCelle et al. | D24/1.1 |
| 4,625,731 A | 12/1986 | Quedens et al. | 128/660 |
| 4,790,610 A | * 12/1988 | Welch et al. | 312/209 |
| 4,793,345 A | 12/1988 | Lehmer | 128/303.13 |
| D300,241 S | 3/1989 | LaCelle et al. | D24/1.1 |
| 4,837,857 A | 6/1989 | Scheller et al. | 455/617 |
| 5,007,688 A | * 4/1991 | Bayerlein et al. | 312/209 |
| 5,112,019 A | * 5/1992 | Metzler et al. | 248/125.2 |
| 5,113,546 A | * 5/1992 | Parent | 15/315 |
| D338,272 S | 8/1993 | Cunagin et al. | D24/167 |
| D352,106 S | 11/1994 | Fanney et al. | D24/185 |
| D355,257 S | * 2/1995 | Nobles | D24/185 |
| 5,399,007 A | * 3/1995 | Marconet | 312/209 |
| 5,518,310 A | * 5/1996 | Ellman et al. | 312/209 |
| D375,553 S | 11/1996 | Creed et al. | D24/111 |
| D376,207 S | 12/1996 | Buczek et al. | D24/172 |
| 5,590,938 A | * 1/1997 | De Andrea | 312/236 |
| D380,550 S | 7/1997 | Dennewill et al. | D24/185 |
| 5,673,985 A | * 10/1997 | Mitchell | 312/223.1 |
| 5,800,396 A | 9/1998 | Fanney et al. | 604/151 |
| 5,857,685 A | * 1/1999 | Phillips et al. | 248/129 |
| 5,873,885 A | 2/1999 | Weidenbenner | 606/171 |
| D410,544 S | 6/1999 | Metzler et al. | D24/172 |
| 5,921,646 A | * 7/1999 | Hwang | 312/249.8 |
| 5,927,835 A | * 7/1999 | Mergold et al. | 297/142 |
| 6,022,088 A | * 2/2000 | Metzler | 312/209 |
| 6,102,497 A | * 8/2000 | Ehr et al. | 280/47.35 |
| D447,567 S | * 9/2001 | Murphy et al. | D24/172 |

OTHER PUBLICATIONS

"The Grieshaber Custom Mobile Equipment Stand", Grieshaber Switzerland, 2/1997, 1 page.

Allergan Sovereign™ Advertisement, *Ocular Surgery News*, Oct. 15, 1999, p. 103.

*CooperVision Surgical—Systems and Supplies*, Copyright 1986, Section 1, "Anterior Segment Systems and Accessories", pp. 1.2 and 1.1.

"The Grieshaber Mobile Equipment Stand", Grieshaber Switzerland, 2/1997, 1 page.

* cited by examiner

CART FOR SURGICAL CONSOLE

This application is a continuation-in-part of U.S. application Ser. No. 29/114,834 filed Dec. 2, 1999, now U.S. Pat. No. D,447,567. This application also claims the benefit of U.S. Provisional Application No. 60/241,120 filed Oct. 17, 2000.

FIELD OF THE INVENTION

The present invention generally pertains to surgical consoles. More particularly, the present invention pertains to carts or other similar apparatus for the storage and transportation of such consoles.

DESCRIPTION OF THE RELATED ART

Various carts for the storage and transportation of surgical consoles are known. Simple, open carts with several, stacked shelves are sometimes used for this application. The carts are typically made from metal or plastic, and may employ solid shelves or shelves formed from spaced, parallel members. Such carts are not specifically designed for the surgical console they serve, and provide little, if any, protection for the ancillary equipment and consumables that are used with the surgical console.

Other carts have been designed for medical applications. These carts typically have an external surface for supporting a surgical console, an internal frame made from metal with shelves and/or drawers to store the ancillary equipment and consumables used with the surgical console, and an outer housing disposed over the internal frame. The outer housing is typically constructed of multiple sheets of sheet metal or multiple plastic components, such as structural foam, fastened together with screws, rivets, or other conventional fastening apparatus. The sheet metal or plastic components are typically painted to provide a chemically resistant and aesthetically pleasing external surface. However, in the operating room environment, the painted sheet metal or plastic components are subject to exposure to a variety of medical and cleaning fluids that are corrosive to the cart. Such fluids can remove paint from the sheet metal or plastic surfaces over time. Such fluids also find their way, through the spaces or seams between the various sheets of sheet metal or plastic components, to the underlying metal frame and electronic apparatus stored therein. The metal frame and electronic apparatus are highly susceptible to corrosion and damage due to exposure to such fluids. All these problems are detrimental to the appearance and useful lives of the cart, surgical console, and the electronic apparatus stored within the cart. These problems are also highly inconvenient to the surgeon and his or her staff.

Therefore, a need exists for an improved cart for a surgical console that does not suffer from the above-described limitations. Ideally, the cart should also be easy for the surgeon and his or her staff to use, and should provide additional functional advantages to the surgeon.

SUMMARY OF THE INVENTION

The present invention is an improved cart for a surgical console. The cart includes a base, an internal frame coupled to the base, and an external housing substantially encasing the internal frame. The external housing comprises a single piece of molded plastic. The external housing prevents operating room fluid ingress into the internal frame. Therefore, the internal frame, its various portions, and the various electronic apparatus and consumables that are stored therein are protected from corrosion and damage.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENT

The preferred embodiment of the present invention and its advantages are best understood by referring to FIGS. 1 through 10 of the drawings, like numerals being used for like and corresponding parts of the various drawings.

Figure 7:
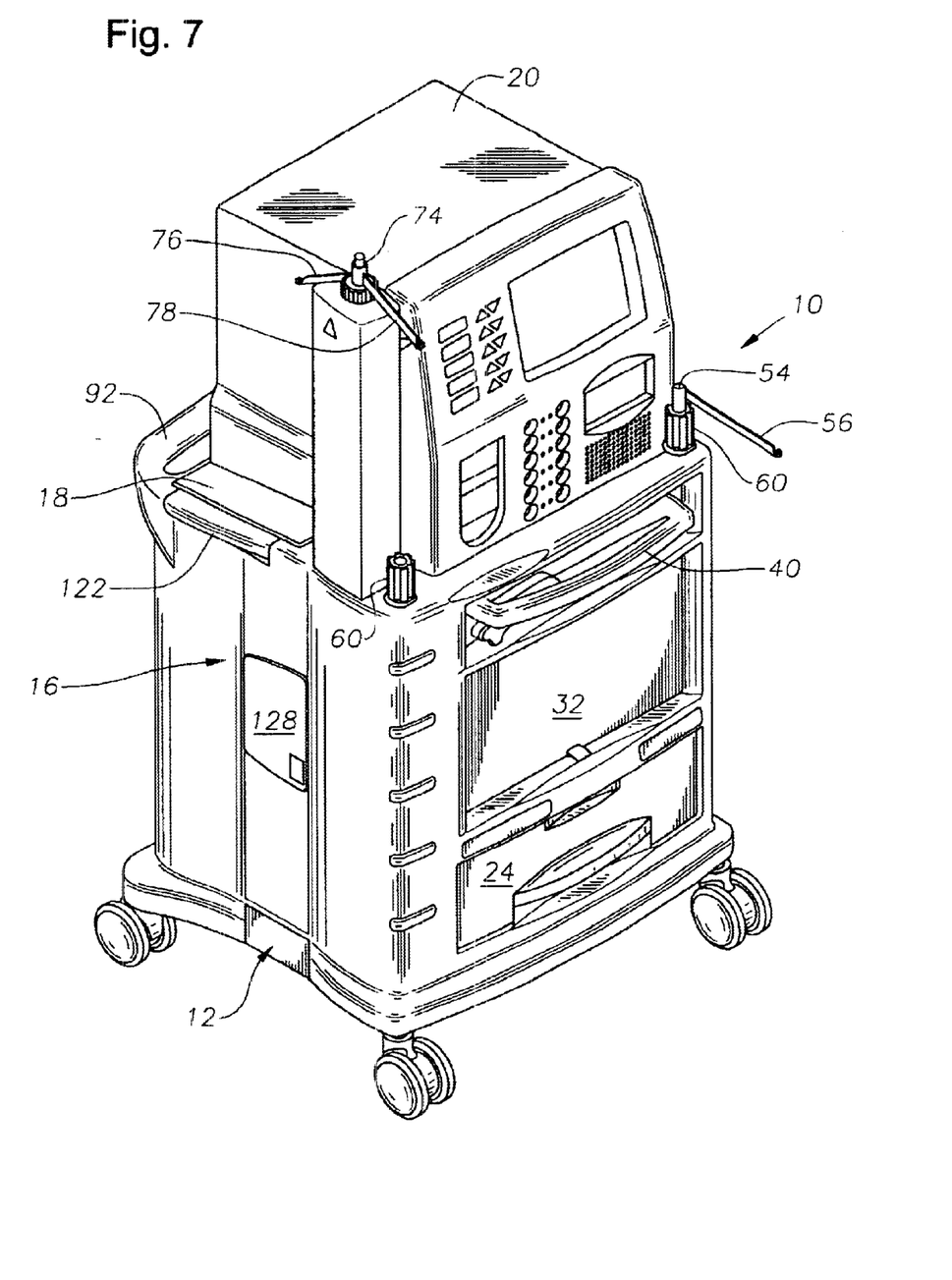
FIG. 7 is a front, perspective view of the cart of FIG. 1 supporting an ophthalmic surgical console.

FIGS. 1–5 show a cart 10 for a surgical console. Cart 10 generally includes a base 12 supporting an internal frame 14, and an external housing 16 that covers internal frame 14. As shown best in FIGS. 1 and 7, external housing 16 has a surface 18 for supporting a surgical console 20. As shown in FIG. 7, surgical console 20 is an ophthalmic surgical console. Although cart 10 is described herein in connection with an ophthalmic surgical console 20, cart 10 may also be used with other surgical consoles or other medical devices.

Returning to FIGS. 1–5, base 12 preferably includes a structural member 19 supported by four caster wheels 20. Structural member 19 is preferably molded from plastic, such as structural foam, and wheels 20 are preferably capable of being locked to prevent rolling. Structural member 19 has a top surface 150.

Internal frame 14 is preferably fastened to structural member 19 via bolts or other conventional fastening apparatus. Frame 14 has a shelf 152, a shelf 154, a top surface 156, a left side surface 158, a right side surface 160, a rear surface 162, and a generally open front. Frame 14 is preferably formed from sheet metal, although plastic or other conventional materials may be utilized. The various portions of internal frame 14 are preferably coupled together with screws, rivets, welding, or other conventional fastening apparatus.

Frame 14 preferably has a first internal volume 22 for receiving a drawer 24. Drawer 24, and the portion of frame 14 forming the sides of volume 22, preferably include conventional sliding drawer rails 26 for slidably disposing drawer 24 within internal volume 22. Drawer 24 is preferably for storing the various electronic apparatus used in connection with console 20, such as, by way of example, a foot pedal or other remote control device, or surgical handpieces.

Figure 1:
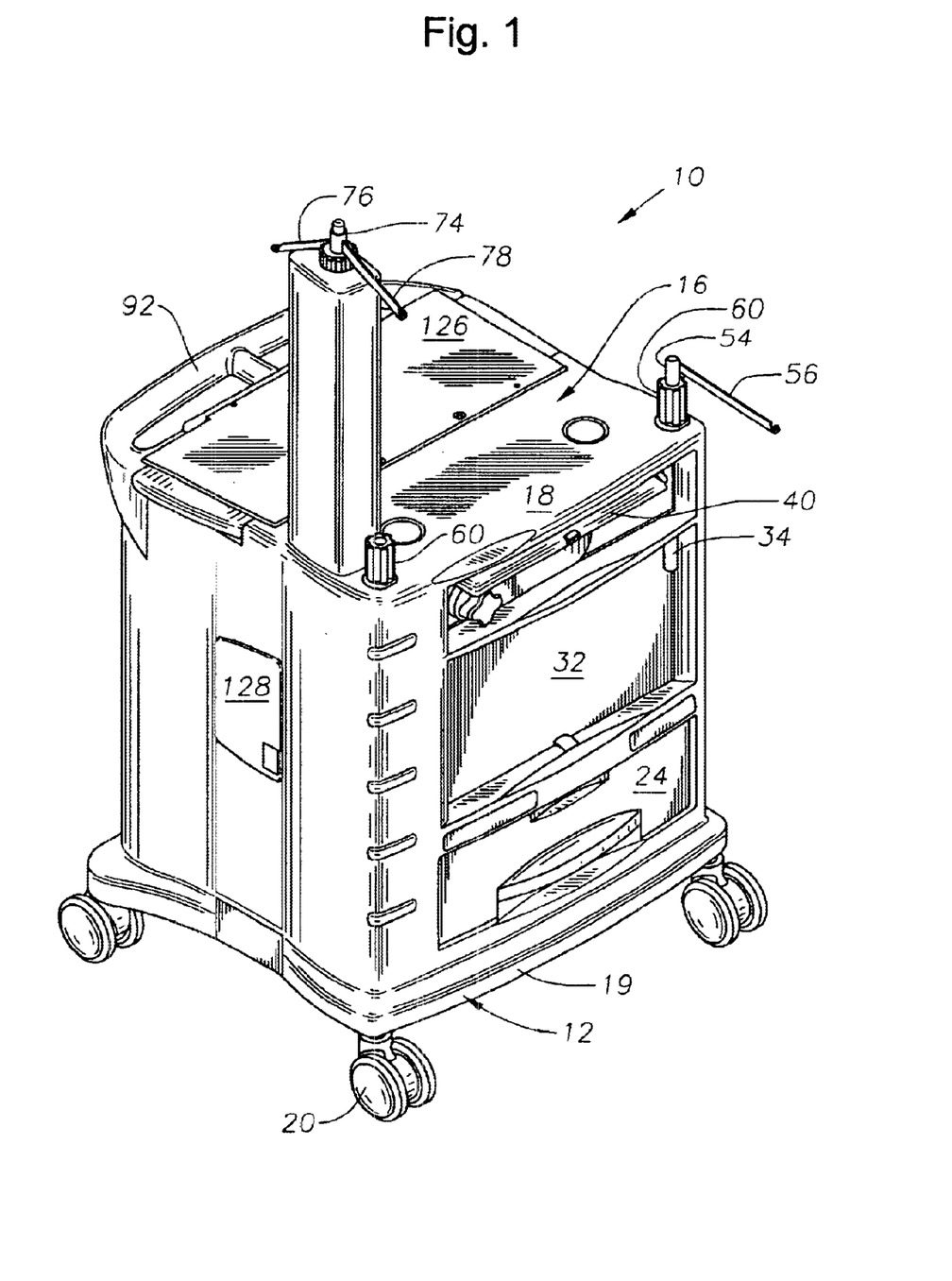
FIG. 1 is a perspective view of the top, front, and left side views of a cart for a surgical console according to a preferred embodiment of the present invention.
Figure 8:
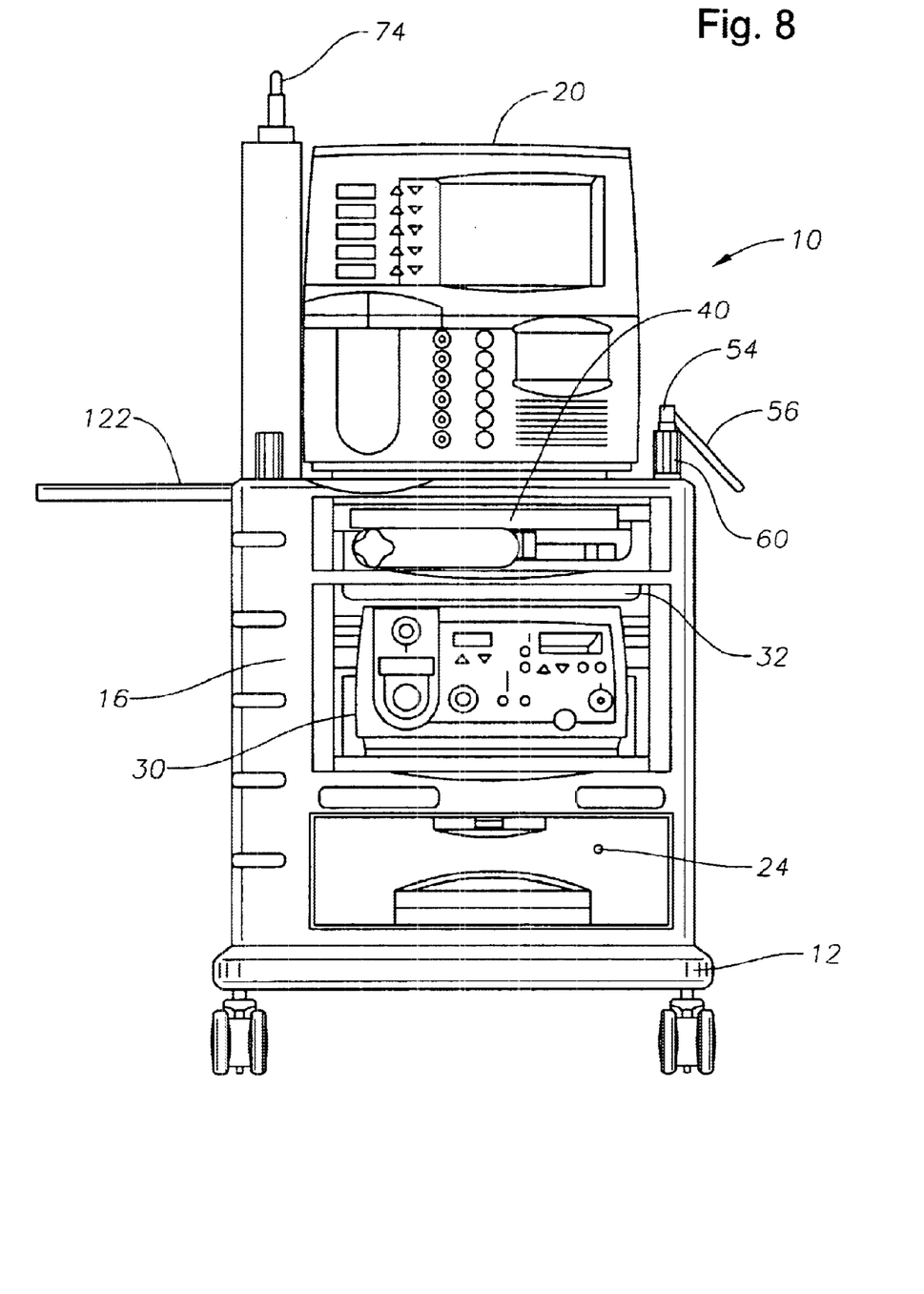
FIG. 8 is a front view of the cart of FIG. 1 supporting a first ophthalmic surgical console on its top surface and storing a second ophthalmic surgical console inside the cart.

Frame 14 preferably has a second internal volume 28. Volume 28 is preferably for receiving a second ophthalmic surgical console 30, as is shown in FIG. 8. As is shown in FIG. 1, a door 32 preferably covers the opening to internal volume 28. Door 32 preferably can be rotated at its upper end 34 and then slid within volume 28 above console 30 via conventional sliding drawer rails 36. Openings 66 and 68 provide ventilation for console 30.

Frame 14 further preferably includes a third internal volume 38 for receiving a tool tray 40. Tool tray 40 is preferably a conventional Mayo tray. As is shown best in FIG. 3, tray 40 is preferably mounted on a telescoping swing arm 42. Swing arm 42 allows tray 40 to be moved from a stored position within internal volume 38, to an extended position for use by the surgeon and his or her staff. Portion 44 and clamping knob 46 of swing arm 42 allow tray 40 to be adjusted to the particular height preferred by the surgeon. As shown best in FIG. 2, third internal volume 38 preferably also receives a second drawer 48. Although not shown in the FIGS., drawer 48, and the portion of frame 14 forming the sides of volume 38, preferably include conventional sliding drawer rails for slidably disposing drawer 48 within internal volume 38. Drawer 48 is preferably used for storing the various consumables used during ophthalmic surgery, such as, by way of example, surgical cassettes, tubing administration sets, drainage bags, and surgical handpiece tips.

Figure 9:
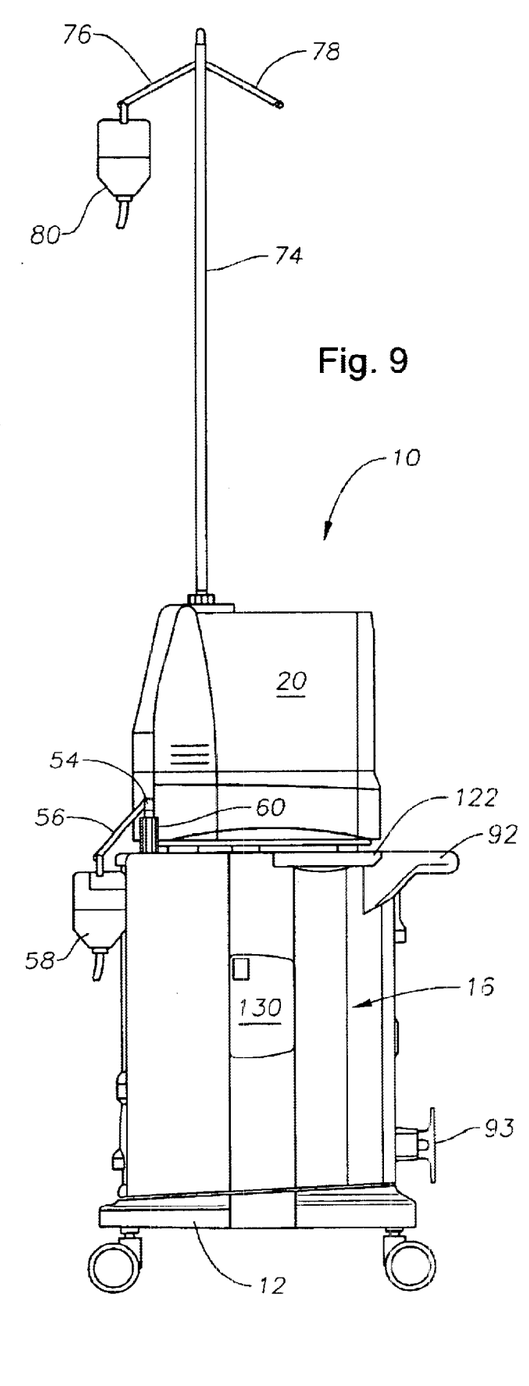
FIG. 9 is a right, side view of the cart of FIG. 1 showing the motorized IV Pole of the cart in an extended position.

Frame 14 preferably includes a housing 50 for receiving a manually adjustable IV pole 54. IV pole 54 has a hanger 56 for a conventional IV bottle 58, which is shown in FIG. 9. IV pole 54 is shown in the FIGS. in its unextended position. However, IV pole 54 may be manually extended to the particular height desired by the surgeon and locked into place using conventional clamping collar 60. Frame 14 also preferably includes a housing 62. Housing 62 may also receive IV pole 54 in the event that a surgeon prefers that pole 54 be disposed on the left side of cart 10. Although not shown in the FIGS., conventional medical grade, flexible tubing providing pressurized air from console 20 may be fluidly coupled to IV bottle 58 so as to provide different infusion pressures for the ophthalmic fluid within IV bottle 58 for use during ophthalmic surgery. One method of providing such different infusion pressures is to use a vented gas forced irrigation/infusion tubing set available from Alcon Laboratories, Inc. of Fort Worth, Tex.

Frame 14 preferably also includes a motorized IV pole assembly 70. Assembly 70 preferably includes a housing 72, an IV pole 74, a hanger 76, and a hanger 78. As shown in FIG. 1, pole 74 is in a completely unextended position. The end of IV pole 74 disposed within housing 72 is coupled to a belt driven lead screw. An electric motor, which is also disposed within housing 72, is rotationally coupled to the lead screw via a belt and pulley system. The electric motor is electronically coupled to console 20 and to sensors that monitor the position of IV pole 74. Such sensors preferably include a printed circuit board having a field programmable gate array to compute the position of IV pole 74, and associated electronics for the command and control of the electric motor, including safety interrupts. By using the graphical user interface of console 20, a surgeon can automatically extend IV pole 74 to a desired height, as shown in FIG. 9. The ophthalmic fluid within IV bottle 80 will then be provided at the desired hydrostatic infusion pressure during ophthalmic surgery.

Figure 5:
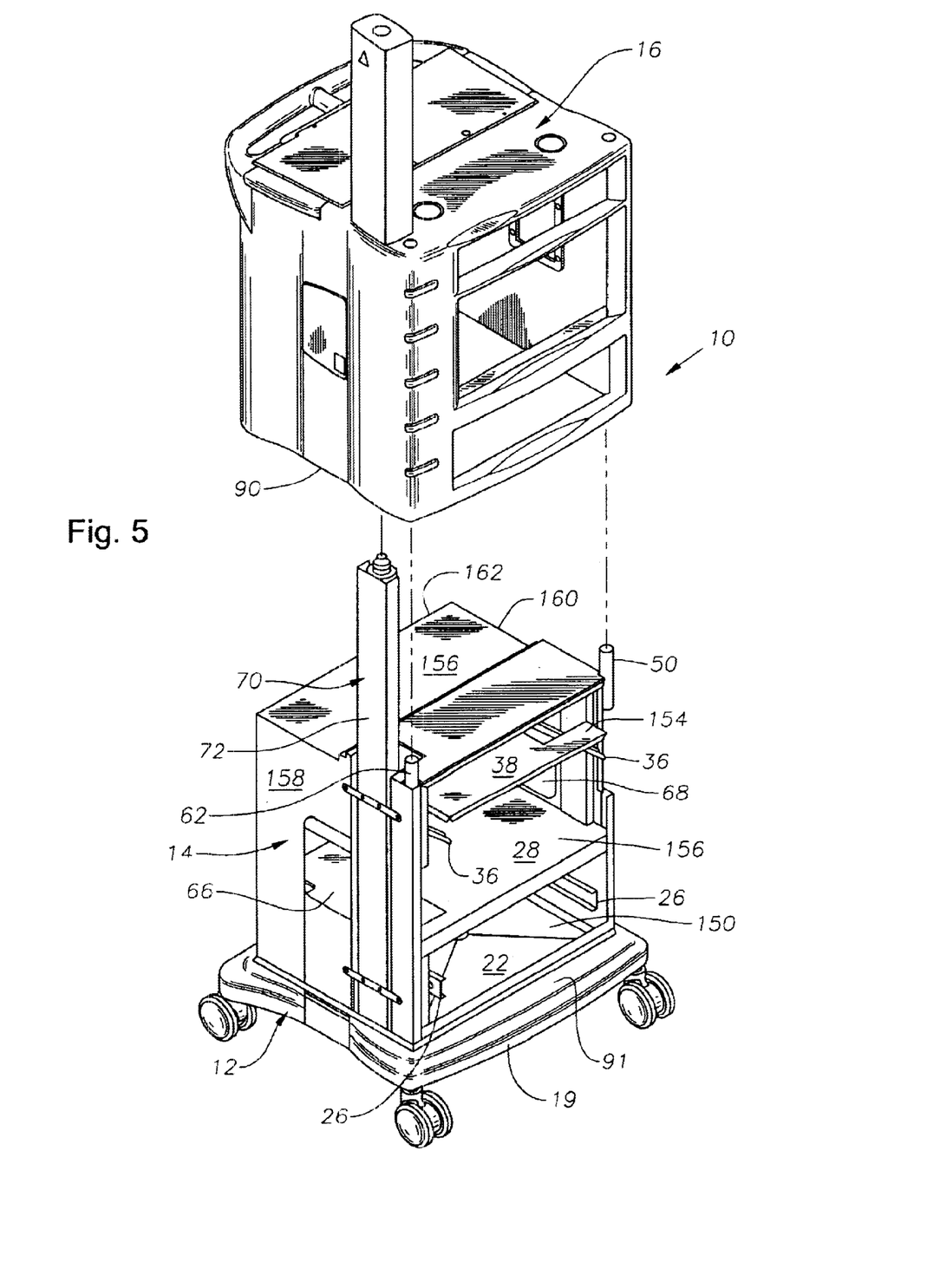
FIG. 5 is a front, perspective, partially exploded view of the cart of FIG. 1 showing the base, internal frame, and external housing of the cart.

As shown best in FIG. 5, external housing 16 is designed to substantially encase and protect internal frame 14, its various components, and the various electronic apparatus and consumables stored within frame 14. Toward that end, the internal geometry of external housing 16 is preferably substantially similar to the external geometry of internal frame 14. The lower portion 90 of housing 16 mates with and rests on the upper portion 91 of structural member 19 of base 12.

Figure 6:
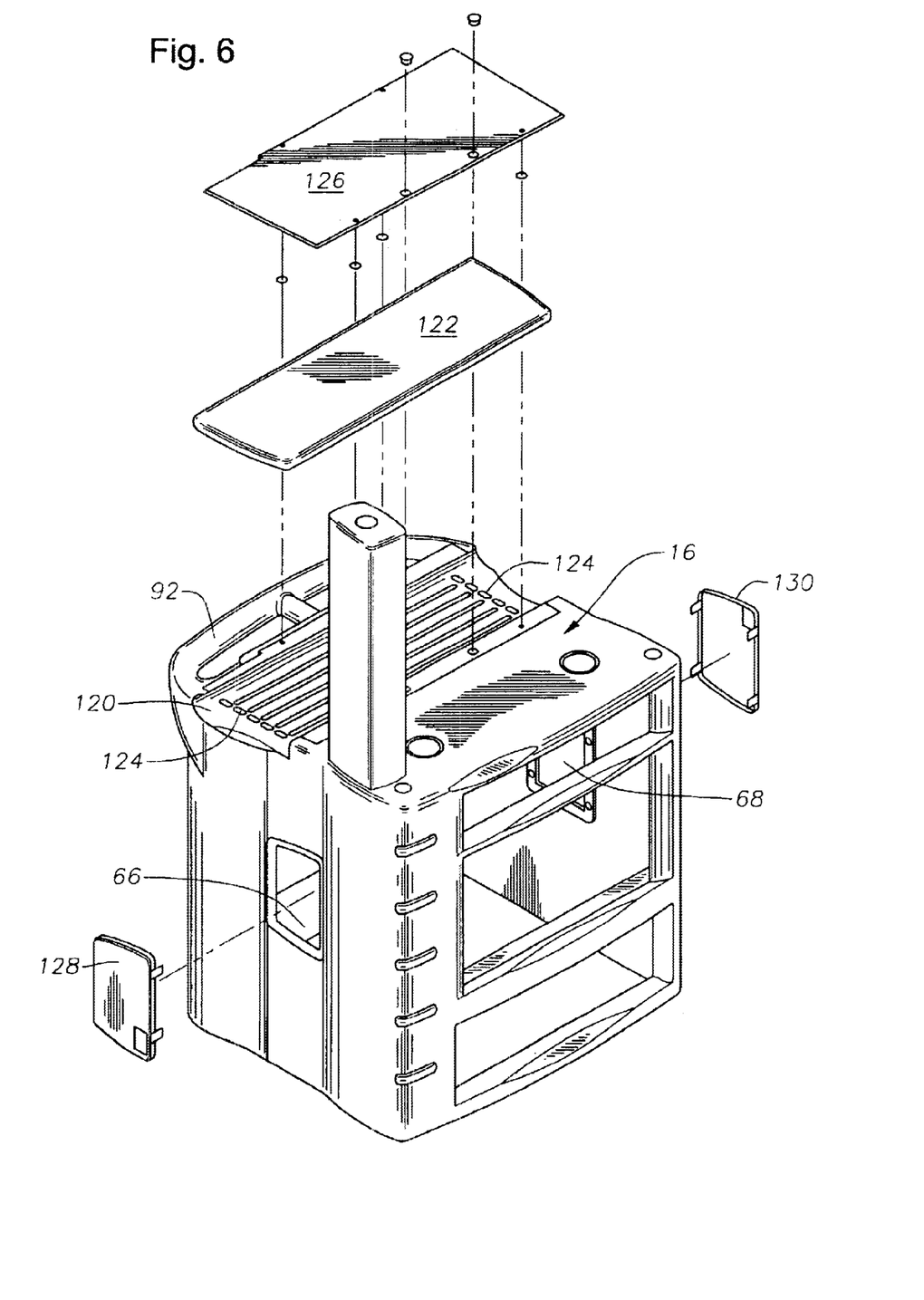
FIG. 6 is a front, perspective, exploded view of the external housing of FIG. 5.

As is best shown in FIG. 6., external housing 16 is preferably molded from a single piece of plastic. Housing 16 is preferably roto-molded from polyethylene. Because housing 16 substantially encases frame 14, and because housing 16 is made from a single piece of plastic, internal frame 14, its various portions, and the electronic apparatus stored within frame 14 are well protected from corrosion or other damage due to exposure to saline solution, detergents, alcohol, disinfecting agents, and other fluids typically used in the operating room environment. In addition, the molded polyethylene plastic of housing 16 does not require painting and can be made in aesthetically pleasing colors.

Figure 2:
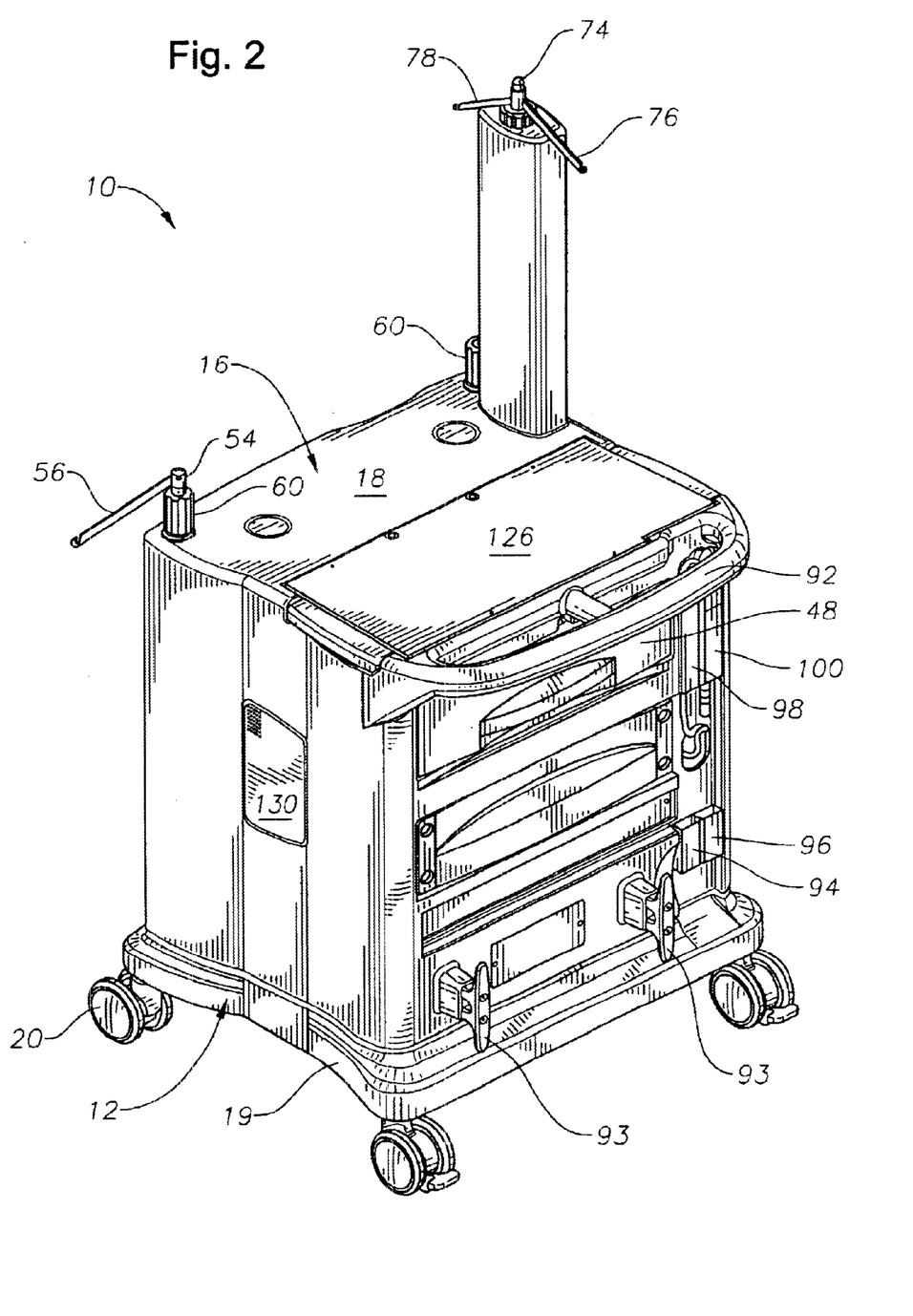
FIG. 2 is a perspective view of the top, rear, and right side views of the cart of FIG. 1.
Figure 3:
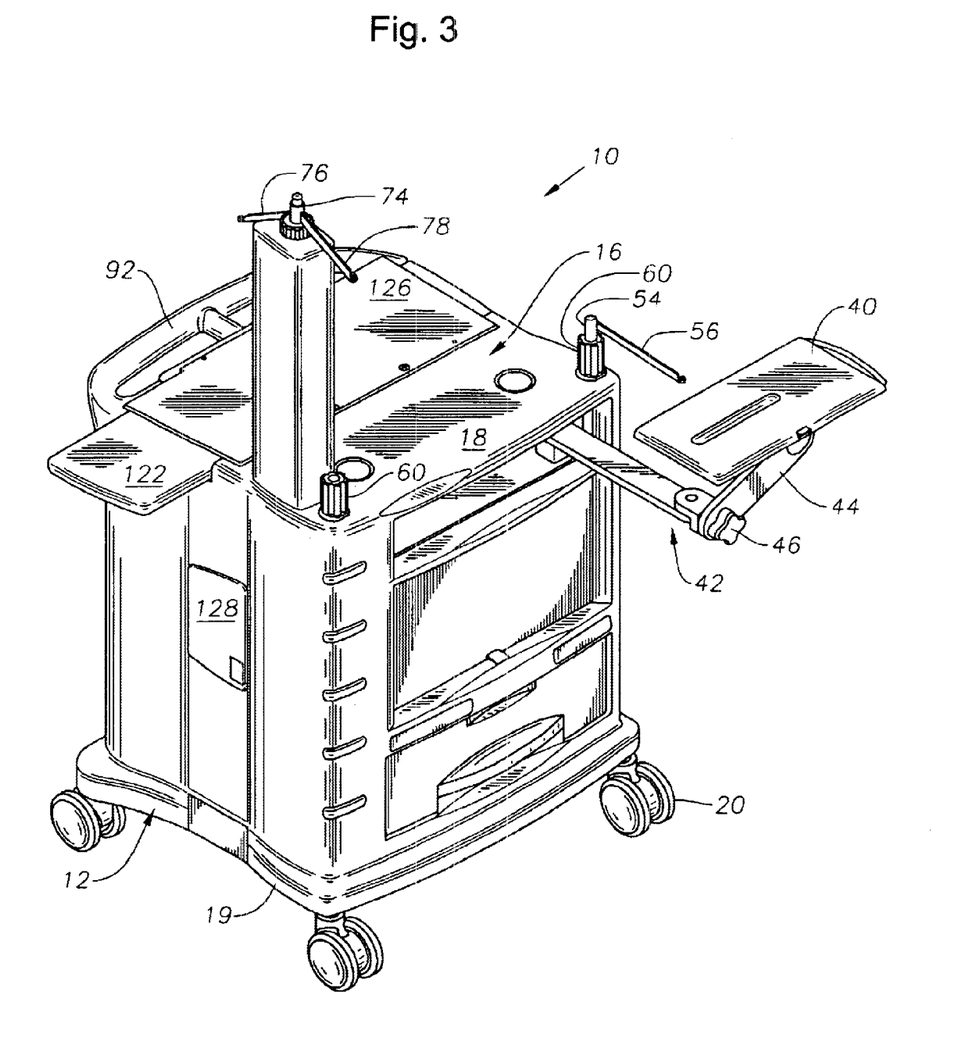
FIG. 3 is a front, perspective view of the cart of FIG. 1 with a telescoping swing arm of a tool tray in an extended position and a work table extended from the left side of the cart.
Figure 4:
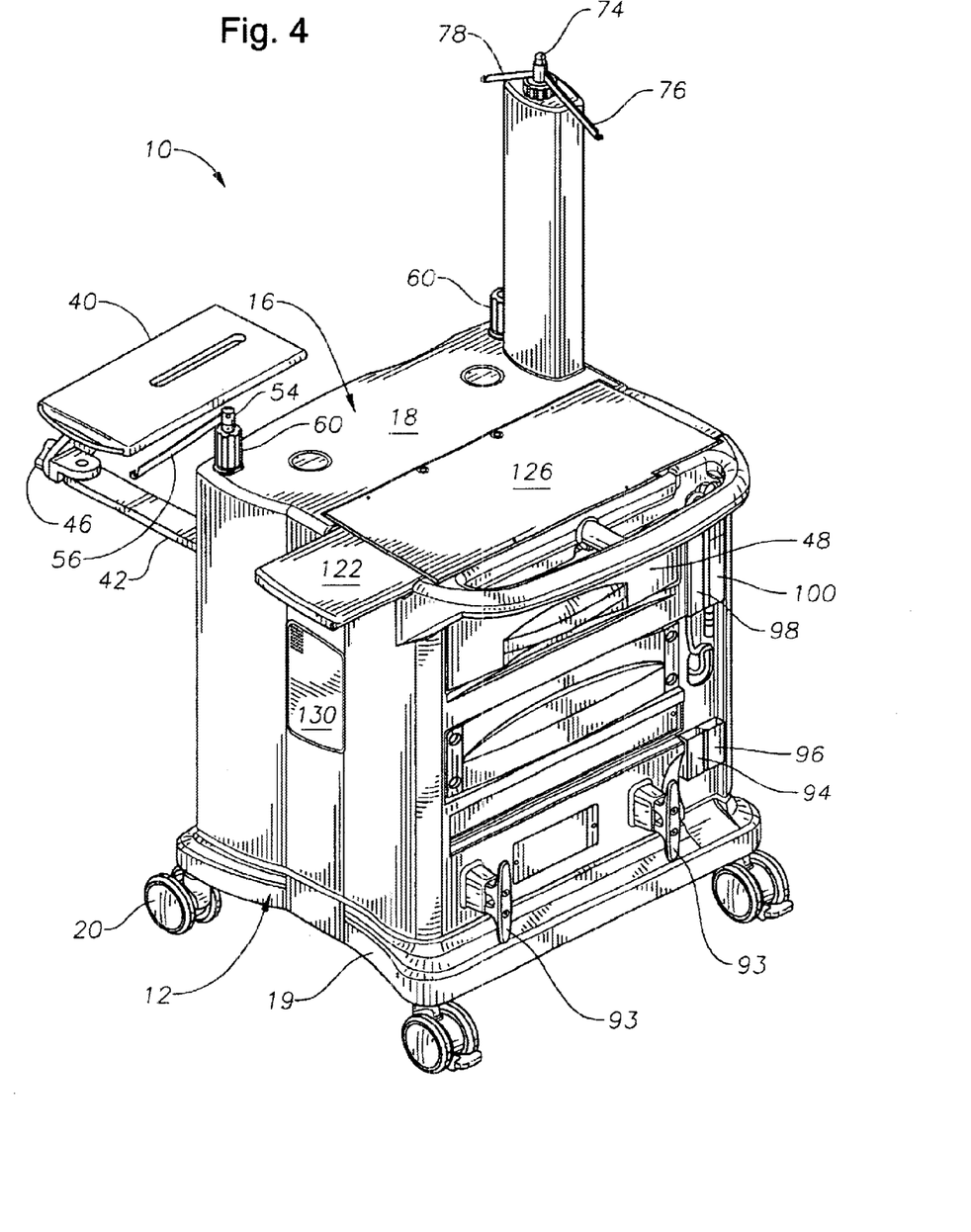
FIG. 4 is a rear, perspective view of the cart of FIG. 1 with the telescoping swing arm of a tool tray in an extended position and a work table extended from the right side of the cart.
Figure 10:
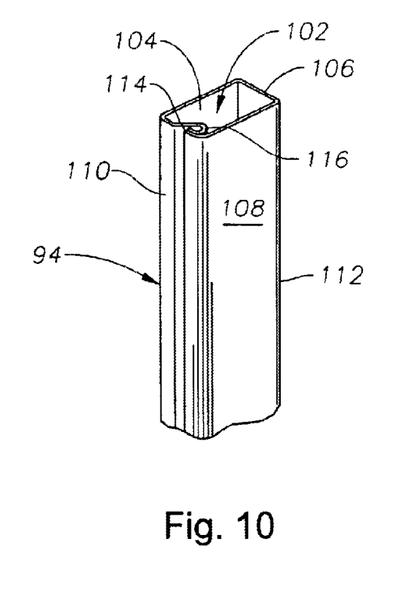
FIG. 10 is a detailed, perspective view of the cable management structures of the cart of FIG. 1.

As is shown best in FIG. 2, housing 16 preferably includes a handle 92 designed to facilitate the movement of cart 10. Cleats 93 preferably provide support for winding and storing cables, tubing, hoses, or similar items from consoles 20 and 30 and their ancillary apparatus. Housing 16 also preferably includes cable management structures 94, 96, 98, and 100 disposed on its rear surface. As shown best in FIG. 10, each of cable management structures 94, 96, 98, and 100 preferably has a generally rectangular geometry and is molded from plastic. Each structure preferably has a hollow bore 102, a rear surface 104, a side surface 106, a cover 108, and a side surface 110. Hollow bore 102 is for receiving and routing the various electronic cables of consoles 20 and 30 and their ancillary electronic apparatus. Cover 108 is naturally hinged to side surface 106 along line 112. Cover 108 also has a curved lip 114. Side surface 110 also has a curved lip 116 designed to frictionally mate with curved lip 114 of cover 108 when cover 108 is in a closed position, as shown in FIG. 10. Lip 114 may be disengaged from lip 116 to allow cover 108 to rotate around line 112, opening the cable management structure. Opening cover 108 of the cable management structure facilitates the routing of electronic cables. Cable management structures 94, 96, 98, and 100 can be utilized to receive and route cables, tubing, hoses, or similar items.

Referring again to FIG. 6., external housing 16 also preferably includes a recess 120 running transversely across upper surface 18 proximate to handle 92. Work table 122 is disposed in recess 120. A series of raised tabs 124 preferably support table 122 off recess 120 to reduce friction and allow table 122 to be easily extended out the left or right side of cart 10, as is shown best in FIGS. 3 and 4. A cover 126 encases table 122 within recess 120. Cover 126 is secured to housing 16 using screws or other conventional fastening apparatus. A porous cover 128 preferably covers ventilation opening 66, and a porous cover 130 preferably covers ventilation opening 68.

In operation, cart 10 provides convenient storage, protection, and transportation of ophthalmic surgical consoles 20 and 30, and their associated electronic apparatus and consumables. Cart 10 allows a surgeon to easily operate consoles 20 and 30 during surgery. The surgeon can use tray 40 for holding surgical handpieces and surgical instruments during surgery. The surgeon can use manual IV pole 54 and/or motorized IV pole assembly 70 to provide a wide range of hydrostatic infusion pressures for ophthalmic surgery. Handle 92 and coaster wheels 20 allow cart 10 to be easily moved around the operating room. External housing 16 effectively prevents fluid ingress, protecting internal frame 14, motorized IV pole assembly 70, and the electronic apparatus stored within frame 14 from corrosion or damage.

It is believed that the operation and construction of the present invention will be apparent from the foregoing description. While the apparatus shown or described above have been characterized as being preferred, various changes and modifications may be made therein without departing from the spirit and scope of the invention as defined in the following claims.

What is claimed is:

1. A cart for a surgical console, comprising:
    a housing having a first surface for supporting a surgical console and a second surface; and
    a management structure coupled to said second surface for receiving and routing cables, tubing, or hoses from said surgical console, said management structure being made from a plastic and comprising:
        a rear surface coupled to said second surface of said housing;
        a first side surface extending from said rear surface and having a lip on a free end;
        a second side surface extending from said rear surface and disposed opposite said first side surface;
        a cover rotationally engaged with said second side surface and having a lip on a free end,
        and a longitudinal bore defined by said rear surface, said first side surface, said second side surface, and said cover;
    wherein said lip of said first side surface frictionally engages said lip of said cover when said management structure in is a closed position, and wherein said lip of said first side surface may be disengaged from said lip of said cover to allow said management structure to be opened.

* * * * *